US012670583B2

(12) United States Patent
Dekel et al.

(10) Patent No.: US 12,670,583 B2
(45) Date of Patent: Jun. 30, 2026

(54) SYSTEMS AND METHODS FOR POLYP SIZE ESTIMATION

(71) Applicant: Given Imaging LTD., Yoqneam (IL)

(72) Inventors: Eyal Dekel, Haifa (IL); Dov Eilot, Yokneam (IL); Dori Peleg, Kiryat Bialik (IL)

(73) Assignee: GIVEN IMAGING LTD., Yoqneam (IL)

( * ) Notice: Subject to any disclaimer, the term of this patent is extended or adjusted under 35 U.S.C. 154(b) by 388 days.

(21) Appl. No.: 18/023,010

(22) PCT Filed: Sep. 5, 2021

(86) PCT No.: PCT/IL2021/051086
§ 371 (c)(1),
(2) Date: Feb. 24, 2023

(87) PCT Pub. No.: WO2022/054049
PCT Pub. Date: Mar. 17, 2022

(65) Prior Publication Data
US 2024/0013375 A1 Jan. 11, 2024

Related U.S. Application Data

(60) Provisional application No. 63/075,782, filed on Sep. 8, 2020.

(51) Int. Cl.
*G06T 7/12* (2017.01)
*A61B 1/00* (2006.01)
(Continued)

(52) U.S. Cl.
CPC ........ *G06T 7/0012* (2013.01); *A61B 1/00045* (2013.01); *A61B 1/041* (2013.01);
(Continued)

(58) Field of Classification Search
None
See application file for complete search history.

(56) References Cited

U.S. PATENT DOCUMENTS

| | | | | |
|---|---|---|---|---|
| 9,412,054 B1 * | 8/2016 | Krupnik | ................. | A61B 1/041 |
| 9,430,706 B1 * | 8/2016 | Peleg | .................... | G06V 20/49 |

(Continued)

FOREIGN PATENT DOCUMENTS

| | | |
|---|---|---|
| CN | 108292366 A | 7/2018 |
| CN | 109447973 A | 3/2019 |

(Continued)

OTHER PUBLICATIONS

Peleg Dori, "Big Data-Small Data: Image Classification for Colorectal Cancer Diagnosis", Mar. 28, 2017 (Mar. 28, 2017), Retrieved from the Internet on Mar. 18, 2022: URL:https://www.imvc.co.il/Portals/38/Peleg%20Dori.pdf.

(Continued)

*Primary Examiner* — Amandeep Saini
*Assistant Examiner* — Caroline Tabancay Duffy
(74) *Attorney, Agent, or Firm* — Carter, DeLuca & Farrell, LLP

(57) ABSTRACT

A computer-implemented method for estimating a size of a suspected polyp in an image includes accessing an image of in at least a portion of a gastrointestinal tract (GIT) captured by a capsule endoscopy device, wherein the image includes a suspected polyp; receiving an indication to an approximated periphery of the suspected polyp in the image; determining, without human intervention, a 3D measurement of the polyp based on peripheral points in the approximated periphery indication; and estimating a size of the suspected polyp based on the determined 3D measurement.

9 Claims, 11 Drawing Sheets

(51) Int. Cl.

| | |
|---|---|
| *A61B 1/04* | (2006.01) |
| *G06T 7/00* | (2017.01) |
| *G06T 7/60* | (2017.01) |

(52) U.S. Cl.

CPC ............ *G06T 7/60* (2013.01); *A61B 1/00039* (2013.01); *G06T 2200/24* (2013.01); *G06T 2207/10068* (2013.01); *G06T 2207/20084* (2013.01); *G06T 2207/30032* (2013.01)

(56) References Cited

U.S. PATENT DOCUMENTS

| | | | | |
|---|---|---|---|---|
| 9,913,575 | B2 * | 3/2018 | Gazdzinski | .......... A61B 5/6861 |
| 2009/0080692 | A1 * | 3/2009 | Moriya | ..................... G06T 7/62 |
| | | | | 345/30 |
| 2015/0065850 | A1 * | 3/2015 | Jia | ......................... G06T 7/0012 |
| | | | | 600/408 |
| 2016/0217573 | A1 | 7/2016 | Lian et al. | |
| 2018/0075599 | A1 * | 3/2018 | Tajbakhsh | ............ A61B 5/4255 |
| 2018/0253839 | A1 * | 9/2018 | Zur | .................. A61B 1/000094 |
| 2019/0019287 | A1 * | 1/2019 | Reda | ....................... G06V 40/14 |
| 2019/0374155 | A1 * | 12/2019 | Wang | ................... A61B 1/2736 |

| | | | | |
|---|---|---|---|---|
| 2020/0143936 | A1 | 5/2020 | Kamon et al. | |
| 2020/0242764 | A1 * | 7/2020 | Aoyama | .............. A61B 5/7275 |
| 2020/0279373 | A1 * | 9/2020 | Hussain | ................. G16H 50/20 |
| 2020/0387706 | A1 * | 12/2020 | Zur | .................. A61B 1/000094 |

FOREIGN PATENT DOCUMENTS

| | | | |
|---|---|---|---|
| CN | 111028219 | A | 4/2020 |
| WO | 2015031641 | A1 | 3/2015 |
| WO | 2017199258 | A1 | 11/2017 |
| WO | 2020079696 | A1 | 4/2020 |

OTHER PUBLICATIONS

International Search Report and Written Opinion of the International Searching Authority issued in corresponding application PCT/IL2021/051083 mailed Apr. 29, 2022 (17 pages).

First Chinese Office Action issued in corresponding Chinese Application No. 202180070936.X dated Jul. 12, 2025, 16 pages.

Chinese Office Action for Application No. 202180070936.X with English translation, 14 pages.

Chinese Third Office Action for Application No. 202180070936.X dated Apr. 1, 2026 with English translation, 8 pages.

* cited by examiner

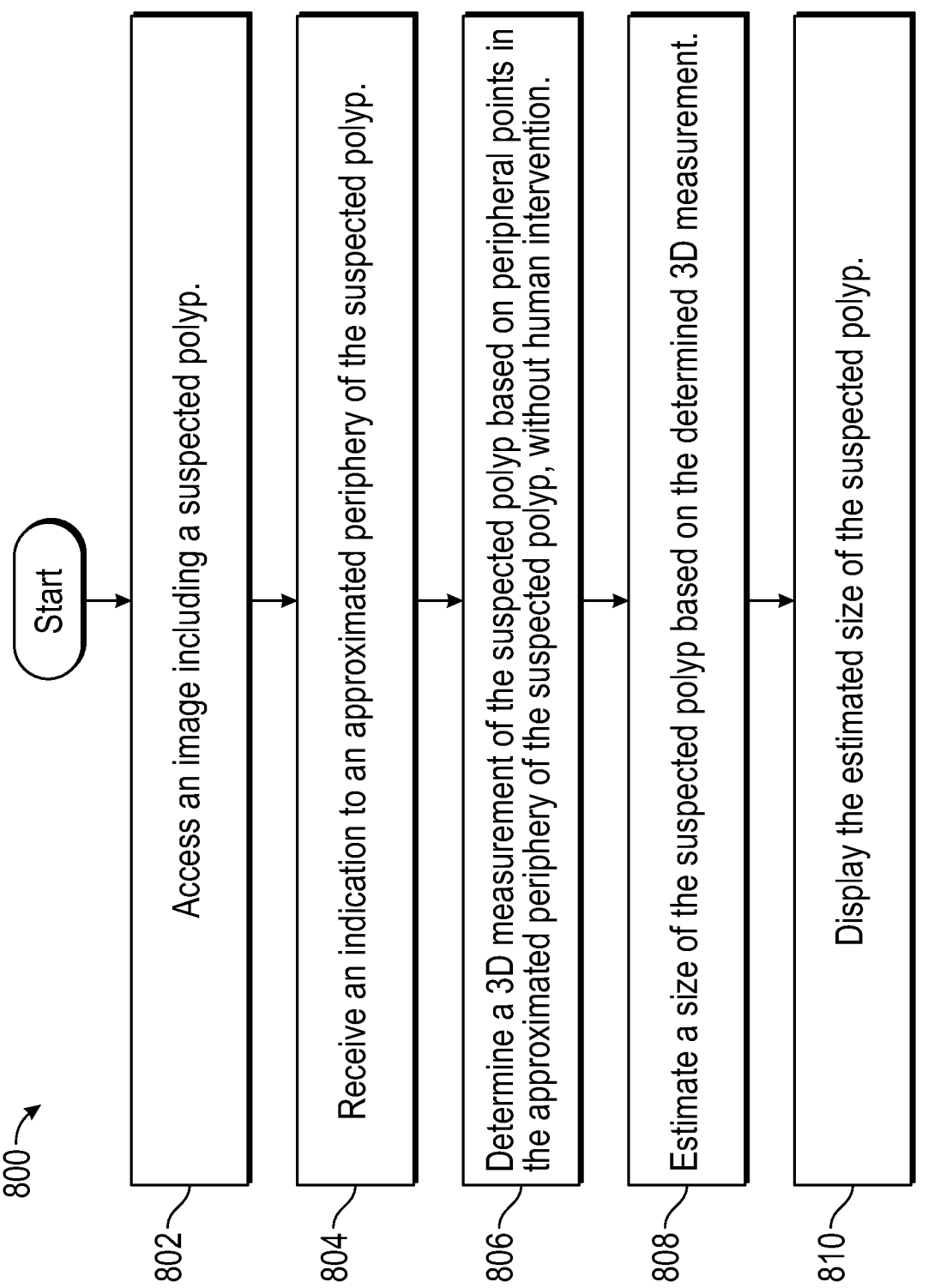

800

Start

802  Access an image including a suspected polyp.

804  Receive an indication to an approximated periphery of the suspected polyp.

806  Determine a 3D measurement of the suspected polyp based on peripheral points in the approximated periphery of the suspected polyp, without human intervention.

808  Estimate a size of the suspected polyp based on the determined 3D measurement.

810  Display the estimated size of the suspected polyp.

FIG. 5

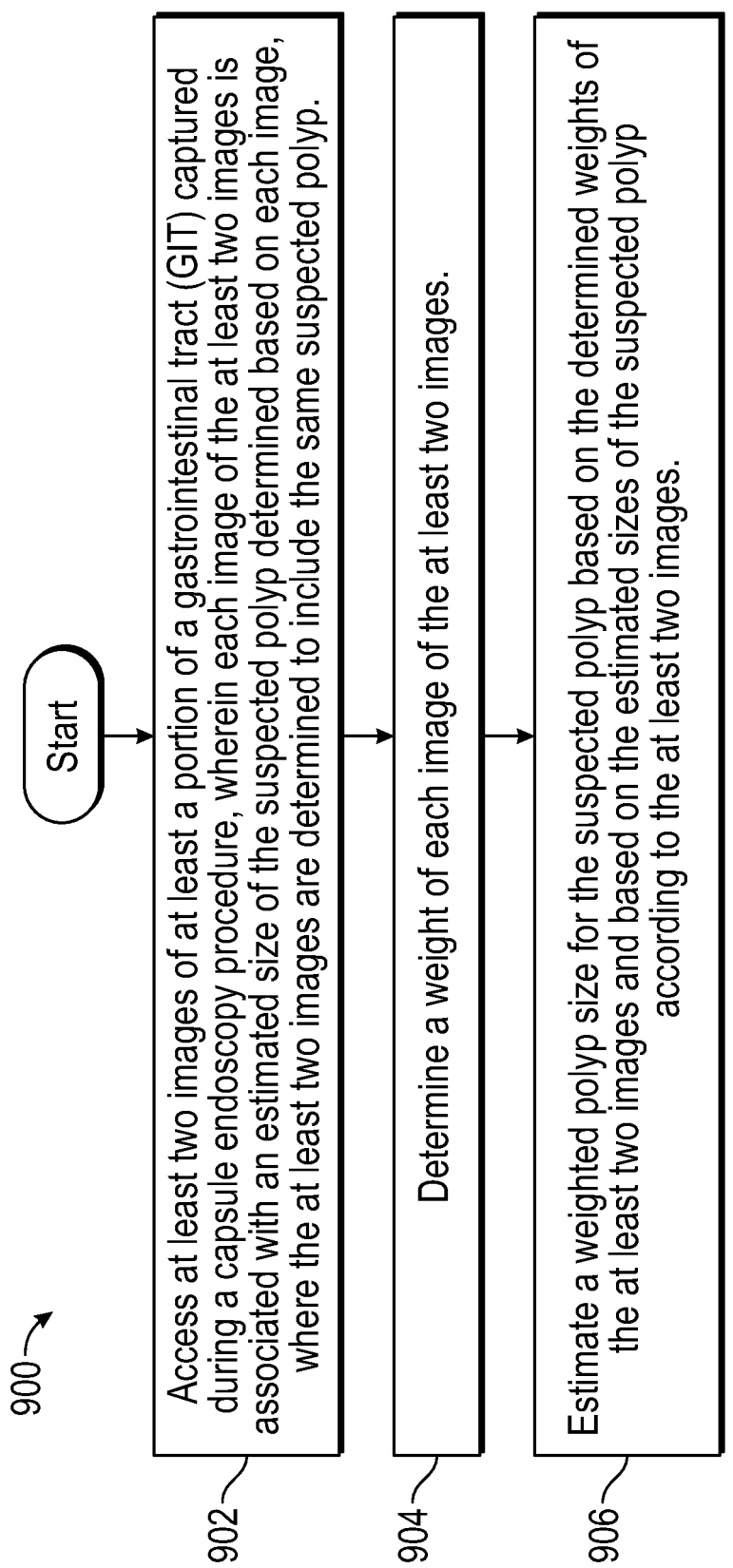

900

Start

902 — Access at least two images of at least a portion of a gastrointestinal tract (GIT) captured during a capsule endoscopy procedure, wherein each image of the at least two images is associated with an estimated size of the suspected polyp determined based on each image, where the at least two images are determined to include the same suspected polyp.

904 — Determine a weight of each image of the at least two images.

906 — Estimate a weighted polyp size for the suspected polyp based on the determined weights of the at least two images and based on the estimated sizes of the suspected polyp according to the at least two images.

SYSTEMS AND METHODS FOR POLYP SIZE ESTIMATION

CROSS-REFERENCE TO RELATED APPLICATION

The present application is a U.S. National Stage Application filed under 35 U.S.C. § 371 (a) claiming the benefit of and priority to International Patent Application No. PCT/IL2021/051086, filed Sep. 5, 2021, which claims the benefit of and priority to U.S. Provisional Application No. 63/075,782, filed Sep. 8, 2020, the entire disclosures of each of which being hereby incorporated by reference herein in its entirety.

FIELD

The disclosure relates to image analysis systems and methods and, more particularly, to systems and methods for analyzing an image including a suspected polyp and estimating the size of the suspected polyp.

BACKGROUND

Capsule endoscopy (CE) allows examining of the entire gastrointestinal tract (GIT) endoscopically using a capsule about the size of a multi-vitamin that is swallowed by the patient. There are capsule endoscopy systems and methods that are aimed at examining a specific portion of the GIT, such as the small bowel (SB) or the colon. CE is a non-invasive procedure that does not require the patient to be admitted to a hospital, and the patient can continue most daily activities while the capsule is in the patient's body.

Typically, a patient is referred by a physician to undergo a CE procedure at a suitable medical facility (e.g., a clinic or a hospital). Upon arrival at the medical facility, the capsule is swallowed by the patient under the supervision of a health professional (e.g., a nurse or a physician) at the medical facility and the patient is provided with a wearable device, e.g., a sensor belt and a recorder placed in a pouch and strap to be placed around the patient's shoulder. The wearable device typically includes a storage device. The patient may be given guidance and/or instructions and then released to proceed with her/his normal daily activities. The capsule captures images as it travels naturally through the GIT. Images and additional data (e.g., metadata) are then transmitted to the recorder that is worn by the patient. The capsule is typically disposable and passes naturally with a bowel movement. The procedure data (e.g., the captured images or a portion of them and additional metadata) is stored on the storage device of the wearable device.

The wearable device is typically returned by the patient to the medical facility with the procedure data stored on the storage device. The procedure data is downloaded from the returned wearable device to a computing device typically located at the medical facility, which stores an engine software. The downloaded procedure data is processed by the engine software to a compiled study (or "study"). Typically, a study includes thousands of images (around 6,000-9,000). Typically, the number of images to be processed is of the order of tens of thousands and about 90,000 images on average.

A reader (which may be the procedure supervising physician, a dedicated physician, or the referring physician) may access the study via a reader software application. The reader then reviews the study, evaluates the procedure, and provides input via the reader software application. Since the reader needs to review thousands of images, the reading time of a study may take between half an hour to an hour on average, often making for a lengthy and tiresome reading task. Following the reading task, a report is generated by the reader software application based on the compiled study and the reader's input. On average, a report takes about one hour to generate. The report may include, for example, images of interest (e.g., images which are identified by the reader as including pathologies), evaluation or diagnosis of the patient's medical condition based on the procedure's data (e.g., the study), and/or recommendations for follow up and/or treatment provided by the reader. The completed report may be forwarded to the referring physician. Based on the received report, the referring physician may decide on a recommended or required follow up or treatment.

The size of a pathology, such as a polyps, a mass or a tumor identified during a CE procedure may influence the diagnosis and treatment (e.g., removal of a polyp via colonoscopy). The size of a pathology having a shape of an ellipsoid or round-like or sphere-like, may be determined based on the length of the axis that has the longest diameter of the pathology (e.g., the major axis or diameter). For example, the size of a colon polyp is measured based on the length of its longest axis. Accordingly, there is a continuing need for systems and methods for automatically estimating the size of a pathology or a suspected pathology identified during a CE procedure.

SUMMARY

The present disclosure relates to systems and methods for analyzing a stream of images of a gastrointestinal tract (GIT), and, more particularly, to systems and methods for analyzing an image including a suspected polyp. More particularly, the present disclosure relates to analyzing an image including a suspected polyp and automatically estimating the size of the suspected polyp. Even though the examples are shown and described with respect to polyps, the disclosed technology can be applied to any ellipsoid or sphere, or round-like pathology.

Further, to the extent consistent, any or all of the aspects detailed herein may be used in conjunction with any or all of the other aspects detailed herein.

Provided in accordance with aspects of the disclosure is a computer-implemented method for estimating a size of a suspected polyp in an image, including accessing an image of at least a portion of a gastrointestinal tract (GIT) captured by a capsule endoscopy device, wherein the image includes a suspected polyp; receiving an indication to an approximated periphery of the suspected polyp in the image; determining, without human intervention, a 3D measurement of the polyp based on peripheral points in the approximated periphery indication; and estimating a size of the suspected polyp based on the determined 3D measurement.

In an aspect of the present disclosure, the method may further include displaying, on a display, the estimated size of the suspected polyp.

In another aspect of the present disclosure, the approximated periphery indication may be generated automatically based on the accessed image or by user input.

In another aspect of the present disclosure, the approximated periphery indication may be generated based on a received mask.

In still another aspect of the present disclosure, determining the 3D measurement of the suspected polyp may further include determining a 3D measurement for every combination of pixels in the periphery and selecting the pair of pixels with the longest 3D measurement.

In yet another aspect of the present disclosure, the method may further include determining a set of extreme pixels among the pixels of the periphery indication in a coordinate system of the image.

In an aspect of the present disclosure, determining the 3D measurement of the suspected polyp may include determining a plurality of most distant pairs of the extreme pixel; for each pair of the plurality of most distant pairs, estimating a 3D length of the suspected polyp based on the pixels of the pair; and selecting a longest estimated 3D length as the determined 3D measurement of the polyp.

In an aspect of the present disclosure, wherein the method may further include displaying, on the display, the set of extreme pixels; receiving input via a user interface indicating a manual correction of the set of extreme pixels; and updating the set of extreme pixels based on the manual correction.

In an aspect of the present disclosure, the 3D length between two pixels of the pair for each pair may be determined by a deep learning system.

In an aspect of the present disclosure, determining the 3D measurement may be based on a tissue model. The tissue model may include a representation of an interaction of tissue with light.

Provided in accordance with aspects of the disclosure is a computer-implemented method for estimating a weighted size of a suspected polyp in an image, including accessing at least two images of at least a portion of a gastrointestinal tract (GIT), captured during a capsule endoscopy procedure, wherein each image of the at least two images is associated with an estimated size of the suspected polyp determined based on each image; determining a weight of each image of the at least two images; and estimating a weighted polyp size for the suspected polyp based on the determined weights of the at least two images and based on the estimated sizes of the suspected polyp of the at least two images.

In an aspect of the present disclosure, the method may further include identifying the accessed at least two images from a plurality of images of the GIT based on a machine learning system.

In an aspect of the present disclosure, the method may further include generating an estimated size of the suspected polyp in each image of the at least two images that include the suspected polyp.

In an aspect of the present disclosure, all of the weights of each image of the at least two images equal 1.

In an aspect of the present disclosure, the weight of each image of the at least two images may be determined based on at least one of: a score indicating a probability of the image including a polyp, a distance of the image from a predefined image, or a cleansing score of the image.

In an aspect of the present disclosure, the method may further include displaying at least one of the weighted size for the suspected polyp or the estimated size for the suspected polyp of an image of the at least two images.

Provided in accordance with aspects of the disclosure is a system for estimating a size of a suspected polyp in an image. The system includes a display, at least one processor, and at least one memory. The at least one memory includes instructions stored thereon which, when executed by the at least one processor, cause the system to access an image of at least a portion of a gastrointestinal tract (GIT) captured by a capsule endoscopy device, wherein the image includes a suspected polyp; receive an indication to an approximated periphery of the suspected polyp in the image; determine, without human intervention, a 3D measurement of the suspected polyp based on extreme points in the approximated periphery indication; and estimate a size of the suspected polyp based on the determined 3D measurement.

In another aspect of the present disclosure, the instructions, when executed by the at least one processor, further cause the system to display, on the display, the estimated size of the suspected polyp.

In another aspect of the present disclosure, the instructions, when executed by the at least one processor, may further cause the system to generate automatically the approximated periphery indication based on the accessed image or by user input.

Provided in accordance with aspects of the disclosure is a computer-implemented method for estimating a size of a suspected polyp in an image, including accessing an image of at least a portion of a gastrointestinal tract (GIT) captured by a capsule endoscopy device, wherein the image includes a suspected polyp; determining, in the image, a plurality of polyp ends along a periphery of the suspected polyp based on a computer vision system; estimating a size of the suspected polyp based on the polyp ends; and displaying, on a display, the estimated size of the suspected polyp.

BRIEF DESCRIPTION OF DRAWINGS

The above and other aspects and features of the disclosure will become more apparent in view of the following detailed description when taken in conjunction with the accompanying drawings wherein like reference numerals identify similar or identical elements.

FIG. 5 is a flow diagram showing a method for estimating the size of a suspected polyp in accordance with aspects of the disclosure;

FIG. 6 is a flow diagram showing a method for estimating a weighted size of a suspected polyp in accordance with aspects of the disclosure;

DETAILED DESCRIPTION

Figure 1:
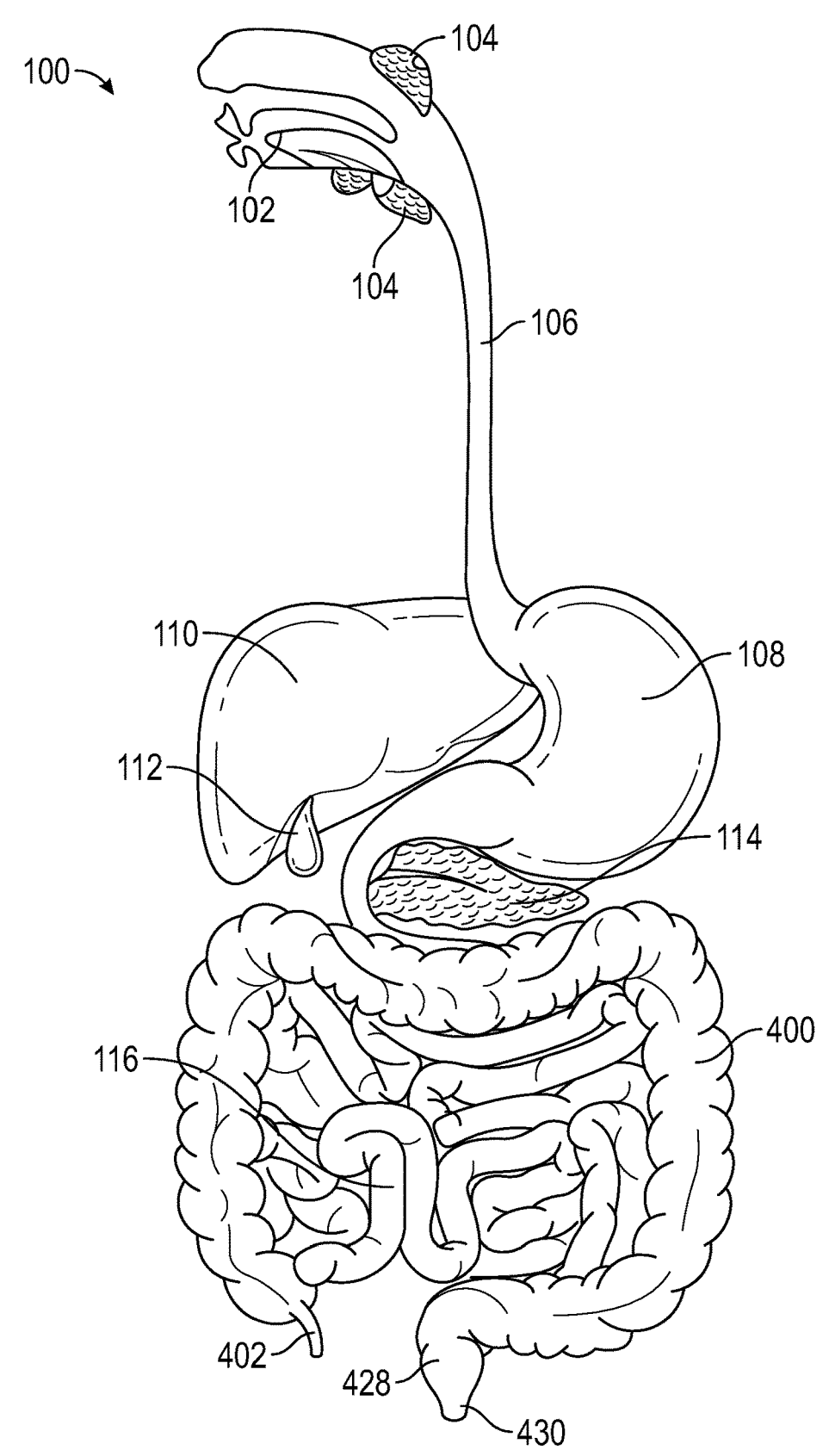
FIG. 1 is a diagram illustrating a gastrointestinal tract (GIT)

The disclosure relates to systems and methods for analyzing medical images and, more particularly, to systems and methods for estimating the size of a suspected polyp in an image captured in vivo via a Capsule Endoscopy (CE) procedure. Even though the examples are shown and described with respect to images captured in vivo by a CE device, the disclosed technology can be applied to images captured by other devices or mechanisms, including anatomical images captured during a colonoscopy procedure or by MRI, for example.

In the following detailed description, specific details are set forth in order to provide a thorough understanding of the disclosure. However, it will be understood by those skilled in the art that the disclosure may be practiced without these specific details. In other instances, well-known methods, procedures, and components have not been described in detail so as not to obscure the present disclosure. Some features or elements described with respect to one system may be combined with features or elements described with respect to other systems. For the sake of clarity, discussion of same or similar features or elements may not be repeated.

Although the disclosure is not limited in this regard, discussions utilizing terms such as, for example, "processing," "computing," "calculating," "determining," "establishing," "analyzing," "checking," or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although the disclosure is not limited in this regard, the terms "plurality" and "a plurality" as used herein may include, for example, "multiple" or "two or more." The terms "plurality" or "a plurality" may be used throughout the specification to describe two or more components, devices, elements, units, parameters, or the like. The term set, when used herein, may include one or more items. Unless explicitly stated, the methods described herein are not constrained to a particular order or sequence. Additionally, some of the described methods or elements thereof can occur or be performed simultaneously, at the same point in time, or concurrently.

The term "location" and its derivatives, as referred to herein with respect to an image, may refer to the estimated location of the capsule along the GIT while capturing the image or to the estimated location of the portion of the GIT shown in the image along the GIT.

A type of CE procedure may be determined based on, inter alia, the portion of the GIT that is of interest and is to be imaged (e.g., the colon or the small bowel ("SB")), or based on the specific use (e.g., for checking the status of a GI disease, such as Crohn's disease, or for colon cancer screening).

The terms "surrounding" or "adjacent" as referred to herein with respect to images (e.g., images that surround another image(s), or that are adjacent to other image(s)), may relate to spatial and/or temporal characteristics unless specifically indicated otherwise. For example, images that surround or are adjacent to other image(s) may be images that are estimated to be located near the other image(s) along the GIT and/or images that were captured near the capture time of another image, within a certain threshold, e.g., within one or two centimeters, or within one, five, or ten seconds.

The terms "GIT" and "a portion of the GIT" may each refer to or include the other, according to their context. Thus, the term "a portion of the GIT" may also refer to the entire GIT, and the term "GIT" may also refer only to a portion of the GIT. The term "clinician" as used herein may include any potential user, such as a physician, e.g., Primary Care Physician (PCP) or gastroenterologist, or a health provider or health professional.

Referring to FIG. 1, an illustration of the GIT 100 is shown. The GIT 100 is an organ system within humans and other animals. The GIT 100 generally includes a mouth 102 for taking in sustenance, salivary glands 104 for producing saliva, an esophagus 106 through which food passes aided by contractions, a stomach 108 to secrete enzymes and stomach acid to aid in digesting food, a liver 110, a gall bladder 112, a pancreas 114, a small intestine 116 (e.g., SB) for the absorption of nutrients, and a colon 400 (e.g., large intestine) for storing water and waste material as feces prior to defecation. The colon 400 generally includes an appendix 402, a rectum 428, and an anus 430. Food taken in through the mouth is digested by the GIT to take in nutrients, and the remaining waste is expelled as feces through the anus 430.

Studies of different portions of the GIT 100 (e.g., SB), colon 400, esophagus 106, and/or stomach 108 may be presented via a suitable user interface. As used herein, the term "study" refers to and includes at least a set of images selected from the images captured by a CE imaging device (e.g., 212, FIG. 2) during a single CE procedure performed with respect to a specific patient and at a specific time, and can optionally include information other than images as well. The type of procedure performed may determine which portion of the GIT 100 is the portion of interest. Examples of types of procedures performed include, without limitation, an SB procedure, a colon procedure, an SB and colon procedure, a procedure aimed to specifically exhibit or check the SB, a procedure aimed to specifically exhibit or check the colon, a procedure aimed to specifically exhibit or check the colon and the SB, or a procedure to exhibit or check the entire GIT: esophagus, stomach, SB and colon.

Figure 2:
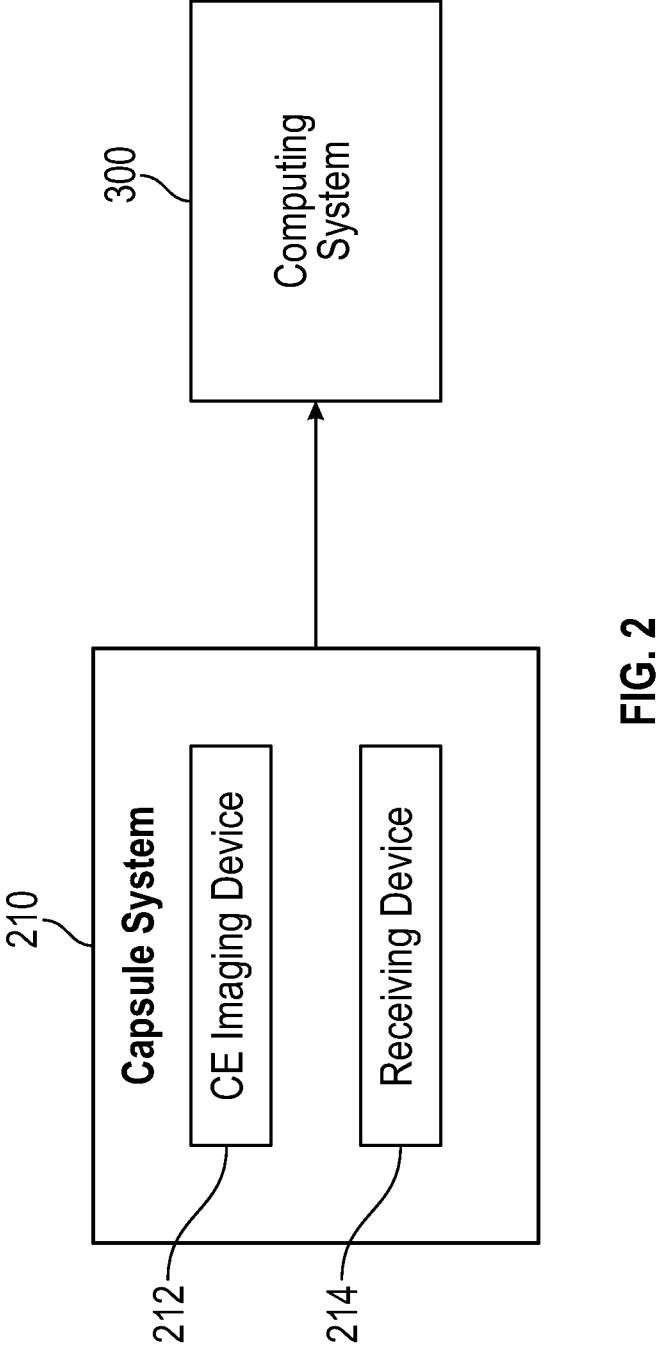
FIG. 2 is a high-level block diagram of an exemplary system for analyzing medical images captured in vivo via a Capsule Endoscopy (CE) procedure in accordance with aspects of the disclosure.

FIG. 2 shows a block diagram of a system 200 for analyzing medical images captured in vivo via a CE procedure. The system generally includes a capsule system 210 configured to capture images of the GIT, and a computing system 300 (e.g., local system and/or cloud system) configured to process the captured images.

The capsule system 210 may include a swallowable CE imaging device 212 (e.g., a capsule) configured to capture images of the GIT as the CE imaging device 212 travels through the GIT. The images may be stored on the CE imaging device 212 and/or transmitted to a receiving device 214, typically including an antenna. In some capsule systems 210, the receiving device 214 may be located on the patient who swallowed the CE imaging device 212 and may, for example, take the form of a belt worn by the patient or a patch secured to the patient.

The capsule system 210 may be communicatively coupled with the computing system 300 and can communicate captured images to the computing system 300. The computing system 300 may process the received images using image processing technologies, machine learning technologies, and/or signal processing technologies, among other technologies. The computing system 300 can include local computing devices that are local to the patient and/or the patient's treatment facility, a cloud computing platform that is provided by cloud services, or a combination of local computing devices and a cloud computing platform.

In the case where the computing system 300 includes a cloud computing platform, the images captured by the capsule system 210 may be transmitted online to the cloud computing platform. In various embodiments, the images can be transmitted via the receiving device 214 worn or carried by the patient. In various embodiments, the images can be transmitted via the patient's smartphone or via any other device connected to the Internet and which may be coupled with the CE imaging device 212 or the receiving device 214.

Figure 3:
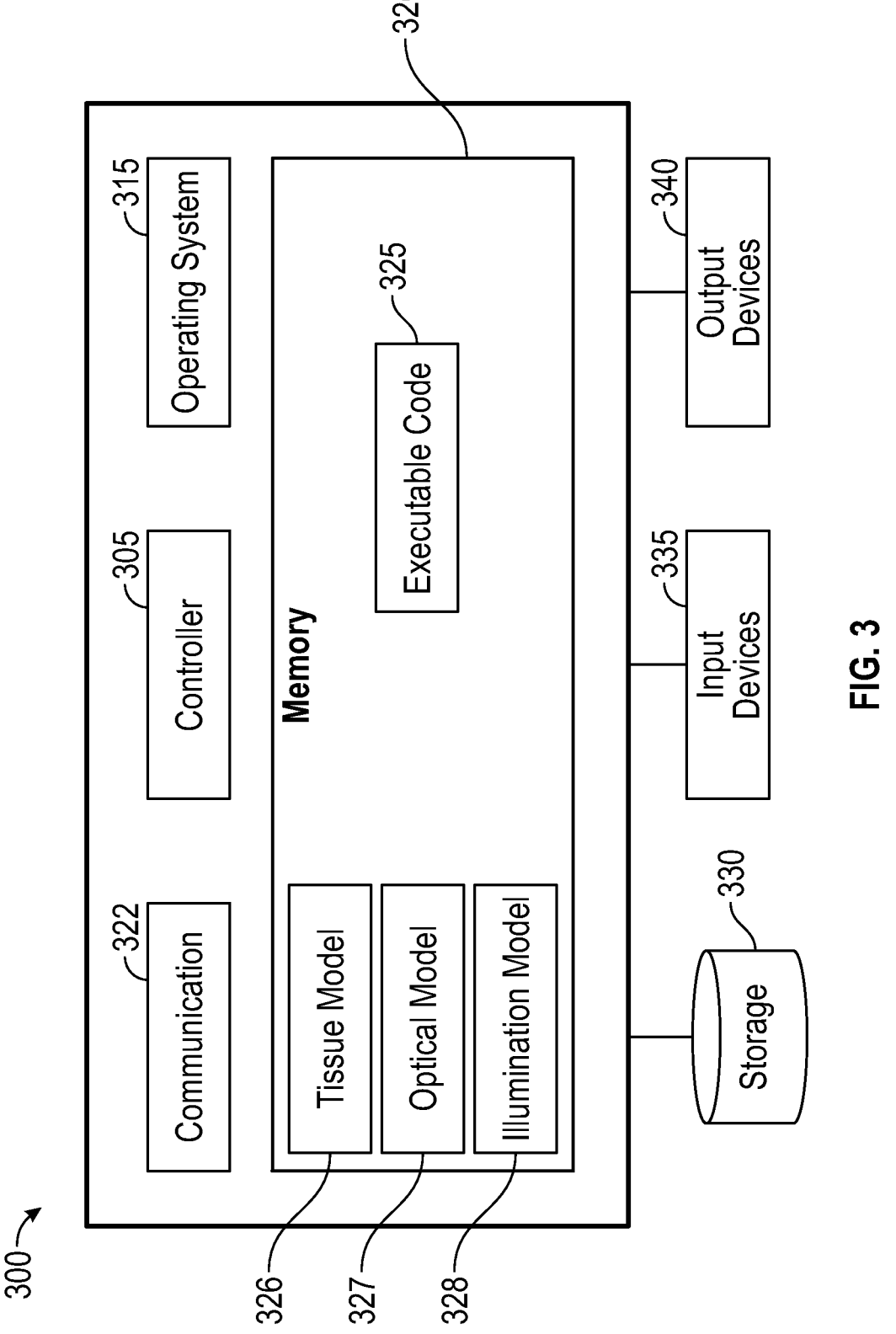
FIG. 3 is a high-level block diagram of an exemplary computing device which may be used with the systems of the disclosure.

FIG. 3 shows a high-level block diagram of an exemplary computing system 300 that may be used with image analyzing systems of the present disclosure. Computing system 300 may include a processor or controller 305 that may be or include, for example, one or more central processing unit processor(s) (CPU), one or more Graphics Processing Unit (s) (GPU or GPGPU), a chip or any suitable computing or computational device, an operating system 215, a memory 320, a storage 330, input devices 335 and output devices 340. Modules or equipment for collecting or receiving (e.g., a receiver worn on a patient) or displaying or selecting for display (e.g., a workstation) medical images collected by the CE imaging device 212 (FIG. 2) may be or include, or may be executed by, the computing system 300 shown in FIG. 3. A communication component 322 of the computing system 300 may allow communications with remote or external devices, e.g., via the Internet or another network, via radio, or via a suitable network protocol such as File Transfer Protocol (FTP), etc.

The computing system 300 includes an operating system 315 that may be or may include any code segment designed and/or configured to perform tasks involving coordination, scheduling, arbitration, supervising, controlling or otherwise managing operation of computing system 300, for example, scheduling execution of programs. Memory 320 may be or may include, for example, a Random Access Memory (RAM), a read-only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 320 may be or may include a plurality of possibly different memory units. Memory 320 may store, for example, instructions to carry out a method (e.g., executable code 325), and/or data such as user responses, interruptions, etc.

Executable code 325 may be any executable code, e.g., an application, a program, a process, task or script. Executable code 325 may be executed by controller 305, possibly under the control of operating system 315. For example, execution of executable code 325 may cause the display, selection for display or analysis of medical images as described herein. In some systems, more than one computing system 300 or components of computing system 300 may be used for multiple functions described herein. For the various modules and functions described herein, one or more computing systems 300 or components of computing system 300 may be used. Devices that include components similar or different to those included in the computing system 300 may be used and may be connected to a network and used as a system. One or more processor(s) 305 may be configured to carry out methods of the present disclosure by for example executing software or code. Storage 330 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, medical images, image streams, etc. may be stored in storage 330 and may be loaded from storage 330 into memory 320 where it may be processed by controller 305. In some embodiments, some of the components shown in FIG. 3 may be omitted.

The memory 320 may further include a tissue model 326, an optical model 327, and/or an illumination model 328, which may be used by an application in order to derive, determine, or estimate a 3D distance as described herein. Tissue model 326, optical model 327, and illumination model 328 may be any suitable code or data. In some aspects, a tissue model may include an optical model, an illumination model, and/or other suitable models. It will be understood that the tissue model, optical model, and illumination model discussed herein may be implemented by any applicable construct or module and may be combined or broken into components as known in the art. For example, these models may be a data structure that may enable an application to search for 3D distance values based on a set of imaging parameters. In other aspects, tissue model 326, optical model 327, and illumination model 328 may further include parameters that may be used by an application in order to derive, determine, or estimate a distance as described herein. For a detailed description of the tissue model, the optical model, and the illumination model, and the used of said models to derive, determine, or estimate a distance, please refer to the patent publication for further details, one or more aspects of which may be included or modified for use with the disclosed aspects, reference may be made to U.S. Pat. No. 9,412,054, the entire contents of which are incorporated herein by reference.

Input devices 335 may include, for example, a mouse, a keyboard, a touch screen or pad, or any suitable input device. It will be recognized that any suitable number of input devices may be operatively coupled to computing system 300. Output devices 340 may include one or more monitors, screens, displays, speakers and/or any other suitable output devices. It will be recognized that any suitable number of output devices may be operatively coupled to computing system 300 as shown by block 340. Any applicable input/output (I/O) devices may be operatively coupled to computing system 300, for example, a wired or wireless network interface card (NIC), a modem, printer or facsimile machine, a universal serial bus (USB) device or external hard drive may be included in input devices 335 and/or output devices 340.

Multiple computer systems 300 including some or all of the components shown in FIG. 3 may be used with the described systems and methods. For example, a CE imaging device 212, a receiver, a cloud-based system, and/or a workstation or portable computing device for displaying images may include some or all of the components of the computer system of FIG. 3. A cloud platform (e.g., a remote server) including components such as computing system 300 of FIG. 3 may receive procedure data such as images and metadata, processes and generate a study, and may also display the generated study for the doctor's review (e.g., on a web browser executed on a workstation or portable computer). An "on-premise" option may use a workstation or local server of a medical facility to store, process and display images and/or a study.

According to some aspects of the present disclosure, a user (e.g., a physician), may build his or her understanding of a case by reviewing a study, which includes a display of images (e.g., captured by the CE imaging device 212) that were selected, e.g., automatically, as images that may be of interest.

Figure 4:
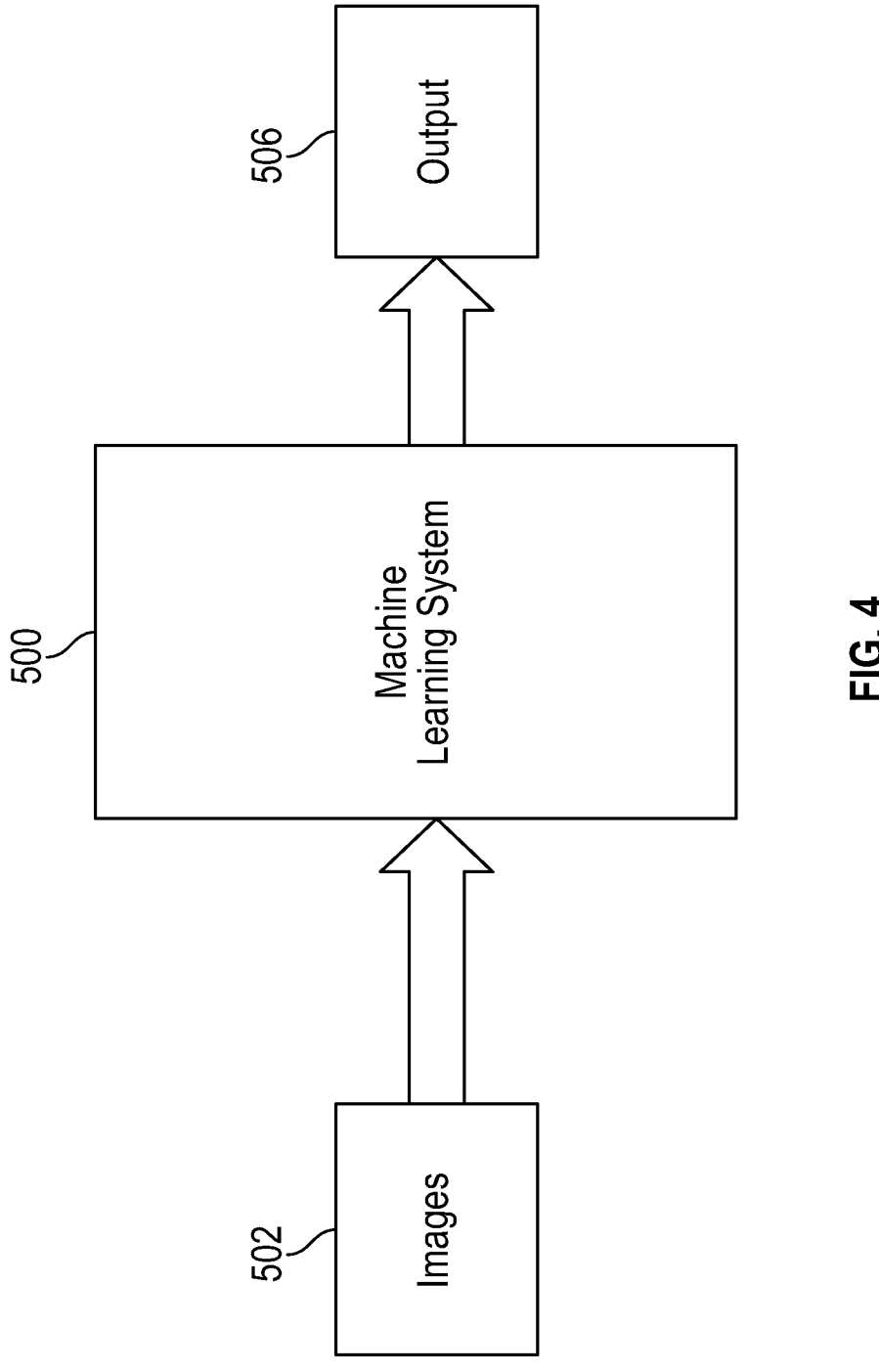
FIG. 4 is a diagram of a machine learning system in accordance with aspects of the disclosure.

With reference to FIG. 4, a block diagram for a machine learning system 500 is shown in accordance with some aspects of the disclosure. The machine learning system 500 may include one or more types of machine learning networks, including, but not limited to classification networks, segmentation networks, and/or deep learning neural networks. Images 502 are input into the machine learning system 500 for processing. The output 506 may change according to the type of the network. In aspects, the machine learning network may generate a polyp probability score (e.g., which may be generated by a classification network). Optionally, a periphery indication may be generated by using a segmentation network. For example, the machine learning system 500 may generate a mask image based on the output of a segmentation network.

Deep learning neural networks used by the disclosed systems and methods may be convolutional neural networks (CNN) and/or a recurrent neural networks. Generally, a deep learning neural network includes multiple hidden layers Deep learning neural networks may be executed on the computer system 300 (FIG. 3). Persons skilled in the art will understand the deep learning neural network and how to implement it.

In machine learning, a CNN is a class of artificial neural network (ANN), most commonly applied to analyzing visual imagery. The convolutional aspect of a CNN relates to applying matrix processing operations to localized portions of an image, and the results of those operations (which can involve dozens of different parallel and serial calculations) are sets of many features that are delivered to the next layer. A CNN may include convolution and deconvolution layers, activation function layers, and/or pooling (typically max pooling) layers to reduce dimensionality without losing too many features. Additional information may be included in the operations that generate these features. Providing unique information that yields features that give the neural networks information can be used to ultimately provide an aggregate way to differentiate between different data input to the neural networks.

Persons skilled in the art will understand training the deep learning neural system 500 and how to implement it.

In some methods in accordance with this disclosure, the machine learning system 500 may be used to generate mask images based on images captured by the CE imaging device 212 (see FIG. 2). A mask image of the polyp (or other anatomical feature) may be generated as an output of one or more of the layers of the machine learning system 500. A probability map (e.g., polyp probability per pixel) may be generated by the machine learning system 500. A mask may be generated based on such a probability map.

The flow diagram of FIG. 5 shows a computer-implemented method 800 for estimating a size of a polyp in an image. Persons skilled in the art will appreciate that one or more operations of the method 800 may be performed in a different order, repeated, and/or omitted without departing from the scope of the disclosure. In some methods in accordance with this disclosure, some or all of the operations in the illustrated method 800 can operate using a capsule endoscopy system, e.g., instrument 212 (see FIG. 2), the receiving device 214 (see FIG. 2), and the computing system 300 (see FIG. 2). Other variations are contemplated to be within the scope of the disclosure. The operations of FIG. 5 will be described with respect to a computing device, e.g., computing system 300 of system 200 (FIG. 2) for analyzing medical images captured in vivo via a CE procedure, or any other suitable computing system device or location thereof, including a remotely-disposed computing device. It will be understood that the illustrated operations are applicable to other systems and components thereof as well. The colon may be used as an example. However, the disclosed methods may apply to images from any portion of the GIT (e.g., suspected polyps in colon or small bowel, a mass, a tumor, or other substantially round or round-like objects in the SB). Even though the examples are shown and described with respect to polyps, the disclosed technology can be applied to any ellipsoid or sphere, or round-like pathology.

Currently, in the field of Capsule Endoscopy, the polyp size measurement is performed at least in part manually. This may cause a large variation between different clinicians (i.e., different clinicians may receive quite different measurements for a suspected polyp in a specified image) and may provide inaccurate size estimations. Thus, a completely or mainly automatic size measurement and estimation provided by the disclosed technology may significantly reduce this difference and allow for a standardized measurement or estimation. For example, according to PillCam© Colon 2 system, the clinician selects two points that define the length of the suspected polyp, and the system provides the measurement of the 3D length for this input pair of points. This measurement then may be determined as the polyp's estimated size. Different clinicians may select different pairs of points which may lead to significantly different size estimations.

A system 200 for analyzing medical images captured in vivo via a CE procedure includes a capsule system 210 configured to capture images of the GIT and a computing system 300 configured to process the captured images. The capsule system 210 may include a swallowable CE imaging device 212 (e.g., a capsule) configured to capture images of the GIT as the CE imaging device 212 travels through the GIT. The images may be stored on the CE imaging device 212 and/or transmitted to a receiving device 214, typically including an antenna. The receiving device 214 receives and may store (e.g., within a storage device in the receiving device) the images. The CE imaging device 212 may include one or more cameras or imaging devices, power source(s), processor(s), and transmitter(s).

Figure 7:
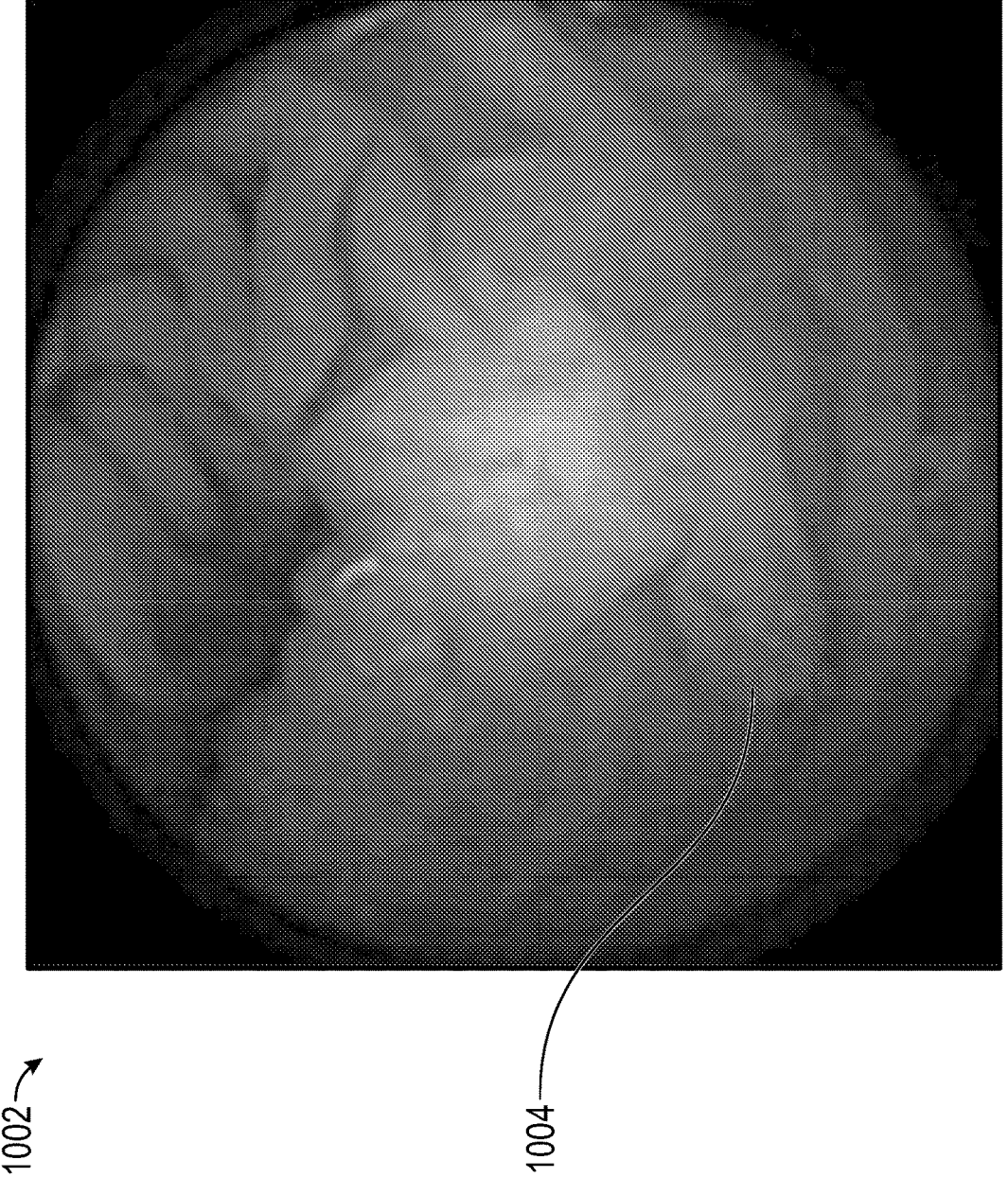
FIG. 7 shows an example image, including a suspected polyp, captured by the system of FIG. 1 in accordance with aspects of the disclosure.

Initially, at step 802, the computing system 300 (e.g., a local or remote system which may be a cloud-based system) accesses an image of at least a portion of a GIT (e.g., a portion of the colon 400), which was estimated or identified to include a suspected polyp captured by a CE device. For example, the accessed image 1002 may include one or more suspected polyps 1004 (FIG. 7).

At step 804, the computing system 300 receives an indication of an approximated periphery of the suspected polyp. The indication includes pixels of the image. In aspects, the approximated periphery indication may be generated based on a mask image. For example, the computing system 300 may receive a mask image 1102 (FIG. 8) based on the accessed image. In aspects, the mask image 1102 may be generated by a deep learning neural network (FIG. 4) or a classical machine learning classifier. The approximated periphery indication may be based on user input. For example, a clinician may delimit the suspected polyp, e.g., on a display by using I/O devices.

For example, a deep learning neural network (e.g., a classification network) may be used for polyp detection (e.g., a polyp detector). The accessed image may be used as an input to another deep learning neural network, e.g., a segmentation network, which may generate a mask image as a byproduct, based on the accessed image.

A mask image, as used herein, includes a binary image consisting of zero and non-zero values. The output of a deep learning neural network may be probability values between 0 and 1 (e.g., a segmentation network), which may be changed into a mask image (e.g., a binary map) based on a threshold value. In aspects, the mask image may be used to obtain the boundary points of the suspected polyp.

In aspects, the computing system 300 may generate the indication to an approximated periphery of the suspected polyp by determine pixels in the accessed image that approximate a periphery 1202 (FIG. 9) of the suspected polyp based on the mask image.

At step 806, the computing system 300 determines, without human intervention, a 3D measurement of the suspected polyp based on peripheral points in the approximated periphery indication. In aspects, the computing system 300 may determine, in the image, a plurality of most distant pairs of pixels (e.g., a plurality of polyp ends) along the periphery of the suspected polyp based on a computer vision system 720. In aspects, the peripheral points may be filtered to reduce the data set and improve processing time and allocation of resources. Next, the computing system 300 may select a longest 3D length as the determined 3D measurement of the suspected polyp.

The computing system 300 may further determine a set of extreme pixels 1204 (FIG. 10) (e.g., end-points) among the pixels that approximate the periphery of the suspected polyp or among the pixels which are included in the indication to the approximated periphery of the suspected polyp. Various methods to determine extreme pixels may be used. For example, the computing system 300 may determine extreme pixels along x-axis and y-axis. For example, the computing system 300 may determine points with the higher distance from the mass center of the suspected polyp. In aspects pixels may be added to the determined extreme pixels by: for each extreme pixel, checking which pixel in the periphery indication is the most distant one—this is performed based on determined 2D distance in the image coordinate system.

In aspects, the extreme polyp pixels (e.g., end-points) may be determined using a blob detector. In image processing, blob detection refers to the use of detectors aimed at detecting points and/or regions in the image that differ in properties like brightness or color compared to the surrounding regions. A blob is a shape in a two-dimensional integer coordinate space where all cells have at least one adjoining cell to the right, left, top, or bottom that is also occupied.

In aspects, the computing system 300 may determine a plurality of most distant pairs, each pair of the plurality of most distant pairs having a corresponding 2D distance. The 2D distance between a pair of points or pixels of the image is determined in the image coordinate system. The computing system 300 may use the 2D distance to reduce the number of queries for 3D length by not querying close-by pairs or querying only pairs having a relatively large distance. For example, computing system 300 may determine a plurality of end-point pairs. To avoid increasing processing time by analyzing all of the plurality of end-point pairs, the computing system 300 may analyze only the pairs with a relatively large 2D distance, since these pairs are the most likely to include the largest 3D length. In aspects, a threshold or a quantity (i.e., select N most distant) may be determined for the 2D distance, to identify or select the pairs with a relatively large 2D distance. In aspects, the pairs of periphery points or periphery pixels are selected from a selected set of points or pixels, e.g., selected outermost or extreme pixels.

In aspects, the computing system 300 may determine a set of outermost extreme pixels among the pixels of the periphery indication in a coordinate system of the image. The determining is performed in the coordinate system of the image. Various methods for determining extreme pixels may include determining extreme pixels along an x-axis and a y-axis, and/or points may be determined with a higher distance from a mass center of the suspected polyp (e.g., predefined N most distant pixels may be selected). One or more methods may be used separately, or in combination, to determine the set of extreme pixels. In aspects, the computing system 300 may filter the pixels that are being analyzed and/or filter the pairs that are checked (e.g., for 3D length) to reduce the dataset and improve processing time and resources consumption.

Next, the computing system 300 may, for each pair of the plurality of most distant pairs, estimate a 3D length based on the pairs with the largest 2D distance. According to some aspects, the computing system 300 may check the 2D distance in the image coordinate system between all possible pairs in the extreme pixels set and select M pairs with the longest 2D distance in the image coordinate system. A 3D measurement will be then determined only for these M selected pairs.

In aspects, when determining the 3D measurement of the suspected polyp, the computing system 300 may determine a plurality of most distant pairs of the pixels of the approximated periphery indication or of the extreme pixels in the coordinate system of the image. Next, the computing system 300 may, for each pair of the plurality of most distant pairs, estimating a 3D length of the suspected polyp based on the pixels of the pair. and select a longest estimated 3D length as the determined 3D measurement of the suspected polyp The computing system 300 may determine the 3D measurement for each pair of points or pixels by calculating, based on a tissue model and/or data associated with the plurality of most distant pairs of the extreme pixels, a distance parameter related to a distance of a suspected polyp from the CE imaging device 212. The 3D measurement may be determined for a set of selected pairs of pixels (according to the methods disclosed) or for all pairs of pixels in the approximated periphery indication. The tissue model may be or may include, for example, a universal tissue model suitable for a plurality of patients; a tissue model specific to a patient condition; and/or a tissue model specific to a region of the GI tract. In aspects, the tissue model may include a representation of an interaction of tissue with light.

For a detailed description of the structure and function of exemplary methods for estimating a 3D length based on 2D points (e.g., pixels), one or more aspects of which may be included or modified for use with the disclosed aspects, reference may be made to U.S. Pat. No. 9,412,054, the entire contents of which are incorporated herein by reference.

In aspects, the estimation of 3D lengths between pixels in the image may include accessing a tissue model, selecting points in the image, determining a distance and/or an estimated distance of the points from CE imaging device 212 based on the tissue model. The operation may derive a geometrical relation associating the point, the distance, and an object and determine a size parameter of the object based on the geometrical relation. As used herein the term "point" includes one or more pixels. In cases where the point includes a plurality of pixels, one pixel, e.g., center pixel, may be selected as presenting the "point" or the point may be presented by averaged pixel values (i.e., averaging the values of all pixels of the "point").

As shown in FIG. 3, a tissue model 326, an optical model 327, and an illumination model 328 may be loaded into memory 320 (other or different models may be used). It will be understood that the tissue model, optical model, and illumination model discussed herein may be implemented by any applicable construct or module and may be combined or broken into components as known in the art. For example, these models may be a data structure that may enable an application to search for distance values based on a set of imaging parameters. The tissue model 326, the optical model 327, and the illumination model 328 may include parameters that may be used by an application in order to derive, determine, or estimate a 3D distance as described herein. For example, an application (e.g., executable code 325 (FIG. 3)) may extract an intensity and color from a pixel in an image and modify these intensity and color values based on data in the illumination model 328 and/or the optical model 327. The application may use the modified values as input into the tissue model 326 in order to estimate a 3D distance of an object represented by the pixel. For example, the illumination model 328 may dictate that a level or percentage of red color extracted from a pixel is to be modified by a factor of 1.03. Based on information related to the light source used by the CE imaging device 212 (FIG. 2) when the relevant image was obtained, it may be necessary to perform such modification prior to estimating a distance using the tissue model 326.

In aspects, the 3D length between two pixels may be determined by a deep learning system.

At step 808, the computing system 300 estimates a size of the suspected polyp based on the determined 3D measurement. In aspects, the computing system 300 may select a longest 3D distance or length as the determined 3D measurement of the suspected polyp.

At optional step 810, the computing system 300 displays the estimated size of the suspected polyp. For example, the computing system 300 may display the accessed image along with the estimated size of the suspected polyp. As another example, the computing system 300 may display the accessed image to a clinician or user, e.g., in the frame of display of a capsule endoscopy study, and display the estimated size only upon request or upon receiving an indication from the clinician or user.

In aspects, the clinician may want to update the set of extreme pixels displayed. The computing system 300 may receive input from a user interface indicating a manual correction of the set of extreme pixels. For example, the clinician may use a mouse or other input and remove one or more pixels from the set of extreme pixels or add one or more pixels to the set on the user interface. The computing system 300 may update the set of extreme pixels based on the input manual correction. In aspects, a clinician may choose a single pair of points, e.g., by drawing a single line by a user interface, on which the computing system 300 may compute the 3D length. The single line may be drawn using a mouse or other similar pointing device or by utilizing a ruler tool, as disclosed in U.S. Pat. No. 9,412,054, the entire contents of which are incorporated herein by reference.

The flow diagram of FIG. 6 shows a computer implemented method 900 for estimating a size of a suspected polyp in an image. Persons skilled in the art will appreciate that one or more operations of the method 900 may be performed in a different order, repeated, and/or omitted without departing from the scope of the disclosure. In some methods in accordance with this disclosure, some or all of the operations in the illustrated method 900 can operate using a capsule endoscopy, e.g., instrument 212 (see FIG. 2), the receiving device 214 (see FIG. 2), and the computing system 300 (see FIG. 2). Other variations are contemplated to be within the scope of the disclosure. The operations of FIG. 6 will be described with respect to a computing device, e.g., computing system 300 of system 200 (FIG. 2) for analyzing medical images captured in vivo via a CE procedure, or any other suitable computing system device or location thereof including a remotely-disposed computing device. It will be understood that the illustrated operations are applicable to other systems and components thereof as well.

At step 902, the computing system 300 accesses at least two images of at least a portion of the GIT, captured during a capsule endoscopy procedure. Each image of the at least two images is associated with an estimated size of the suspected polyp determined based on each image. The at least two images may include the image (a "seed" image) and one or more images which were identified or are determined to include the same suspected polyp. In aspects, the one or more images may be images adjacent to the image (the "seed" image), including the suspected polyp, e.g., a sequence of images (preceding and following the seed image). For example, a "seed" image is selected (e.g., an image from the CE study presented to the user), having an estimated size, and then images which include the same suspected polyp are identified using, for example, a polyp tracker in adjacent images, or for example, an already such generated track is used. For a detailed description of the structure and function of exemplary methods (e.g., tracking and/or classification via machine learning), for identifying if two images include the same pathology (e.g., such as a polyp), one or more aspects of which may be included, or modified for use with the disclosed aspects, reference may be made to U.S. Patent Application No. 63/073,544, filed on Sep. 2, 2020, the entire contents of which are incorporated herein by reference.

The estimated size of the polyp may be generated, for example, according to the computer-implemented method 800 (FIG. 5) for estimating a size of a polyp in an image. It is contemplated that any other known method for generating an estimated size of a polyp in an image may be used. For each image in the plurality of images in which the suspected polyp appears, an estimated polyp size may be calculated according to the method above. It is contemplated that the computing system 300 may use the probability for each frame to include a polyp as a weight and may weigh the probability for each frame together into one size estimate for a suspected polyp.

The identification may include machine learning (e.g., an object tracking algorithm) or may be manually identified by a clinician. For example, an object tracking algorithm may be used that will track and identify the candidate polyp in the preceding images and the following images of the plurality of images. In aspects, the object tracking algorithm may be based on optical flow techniques. The object tracking algorithm may utilize the masks that a polyp segmentation algorithm provides. For example, the operation may visualize the same suspect area (e.g., an area including the same suspected polyp) of each of the images of the at least two images and compare multiple measurements of the same suspected areas. Such object tracking techniques may be performed, for example, based on machine learning techniques. For a detailed description of the structure and function of exemplary methods for object tracking techniques, one or more aspects of which may be included, or modified for use with the disclosed aspects, reference may be made to U.S. Patent Application No. 63/018,870, filed on May 1, 2020, the entire contents of which are incorporated herein by reference.

In aspects, the computing system 300 may receive at least two images that include the same suspected polyp (e.g., different images of the same suspected polyp). The computing system 300 may receive size estimations associated with the different images of the same suspected polyp and determine weights based on the received at least two images.

The computing system 300 may estimate a size of the suspected polyp in each image of the at least two images that include the suspected polyp. For example, the estimated size of the suspected polyp may be accessed from the computer-implemented method 800 (FIG. 5) for estimating a size of a suspected polyp in an image. For example, for each image in the at least two images in which the suspected polyp appears, an estimated polyp size may be calculated according to the method above.

At step 904, the computing system 300 determines a weight of each identified image of the at least two images. In aspects, the weight may be determined based on parameters or characteristics of the image, which may affect the extent of credibility of reliability of the estimates size of the suspected polyp in the image. In aspects, a weight may be a normalized polyp detector score. For example, a size of the polyps in the identified images may be estimated. For example, the polyp sizes may be: 2.9 mm, 5.4 mm, and 6 mm. In aspects, the computing system may access or determine normalized probabilities for the identified images to include polyps, for example: 0.05, 0.85, and 0.1. Thus, the weighted estimates size would be: 2.9*0.05+5.4*0.85+ 0.1*6. Accordingly, an estimated polyp size of a suspected polyp in an image, which has a higher probability to include a polyp (i.e., that the suspected polyp is actually a polyp), would receive a higher weight than an estimated size of the suspected polyp in an image which has a lower probability to include a polyp and in a relative manner. For example, weights may have a zero value if the probability received from a polyp detector is below a threshold of 0.9. In aspects, the weight of the seed image is doubled. In aspects, all of the images of the at least two images may be assigned with an equal weight and the arithmetic mean of all the estimated sizes may be calculated and determined as the weighted estimated size. In aspects, the weight of each image of the at least two images may be determined based on a polyp detector score (i.e., indicating the probability of the image including a polyp), a distance of the image from a predefined image (e.g., the "seed" image), and/or a cleansing score of the image.

At step 906, the computing system 300 estimates a weighted polyp size for the polyp based on the determined weights and the estimated sizes for the suspected polyp of the at least two images. In aspects, the weights may be used to determine a weighted polyp size by multiplying the weight by the polyp size.

For example, an "Average PSE" (average polyp size estimation) may be displayed for each image, which may have, for example, one or more digit(s) after the decimal point. The estimated polyp size may be drawn and indicated on each of the images. For example, the "Average PSE" can be about 6.3 mm, and the estimates suspected polyp size can be 5.5 mm. The clinicians may be encouraged to explore the images associated with the "Average PSE" and assess if the suspected polyp appears larger in other images.

Figure 8:
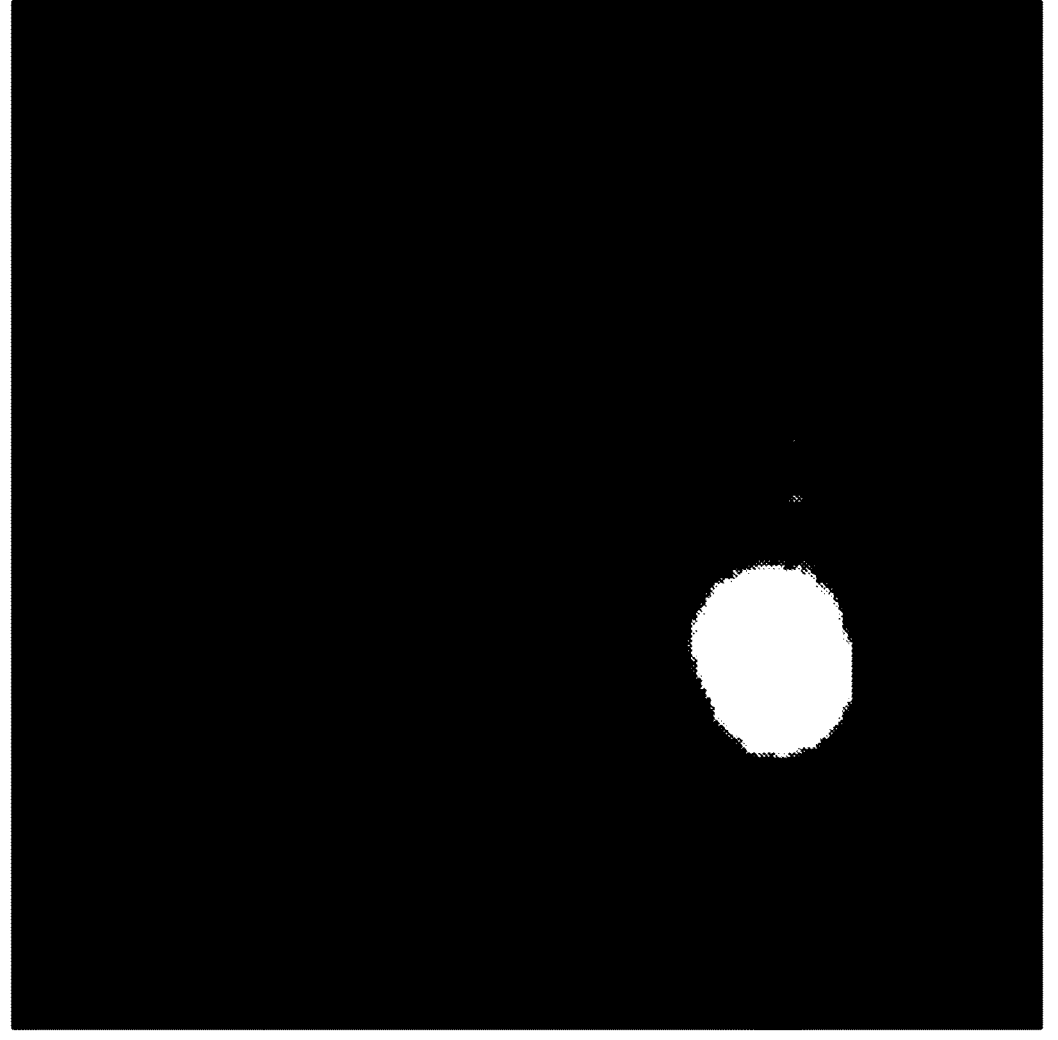
FIG. 8 shows a mask of the example image of FIG. 7 in accordance with aspects of the disclosure.

With reference to FIG. 7, an image 1002 of a portion of the GIT, including a polyp 1004 is shown. Referring to FIG. 8, a mask image 1102 is shown. Generally, a mask image is a binary image, where a feature such as the polyp 1104 of FIG. 7 may include pixels with a zero (e.g., white) value and the remaining portions of the image include pixels with a value of 1 (e.g., black).

Figure 9:
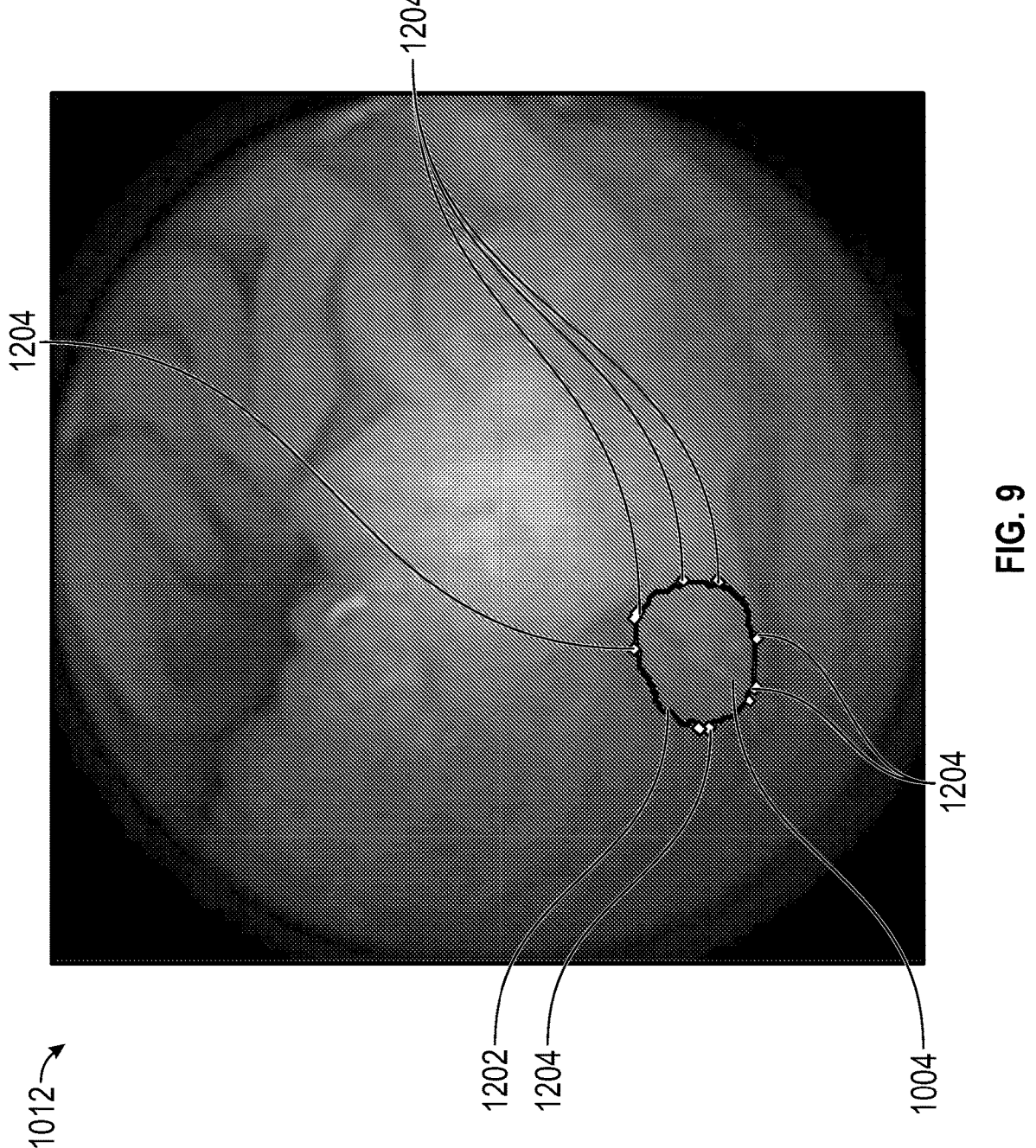
FIG. 9 shows an image with a set of extreme pixels for determining the size of a suspected polyp in accordance with aspects of the disclosure.

Referring now to FIG. 9, an image 1012 indicating the periphery 1202 of the polyp 1004 is shown. The image further shows the extreme pixels 1204, which are used by the disclosed systems and methods to determine a 2D and/or 3D length.

Figure 10:
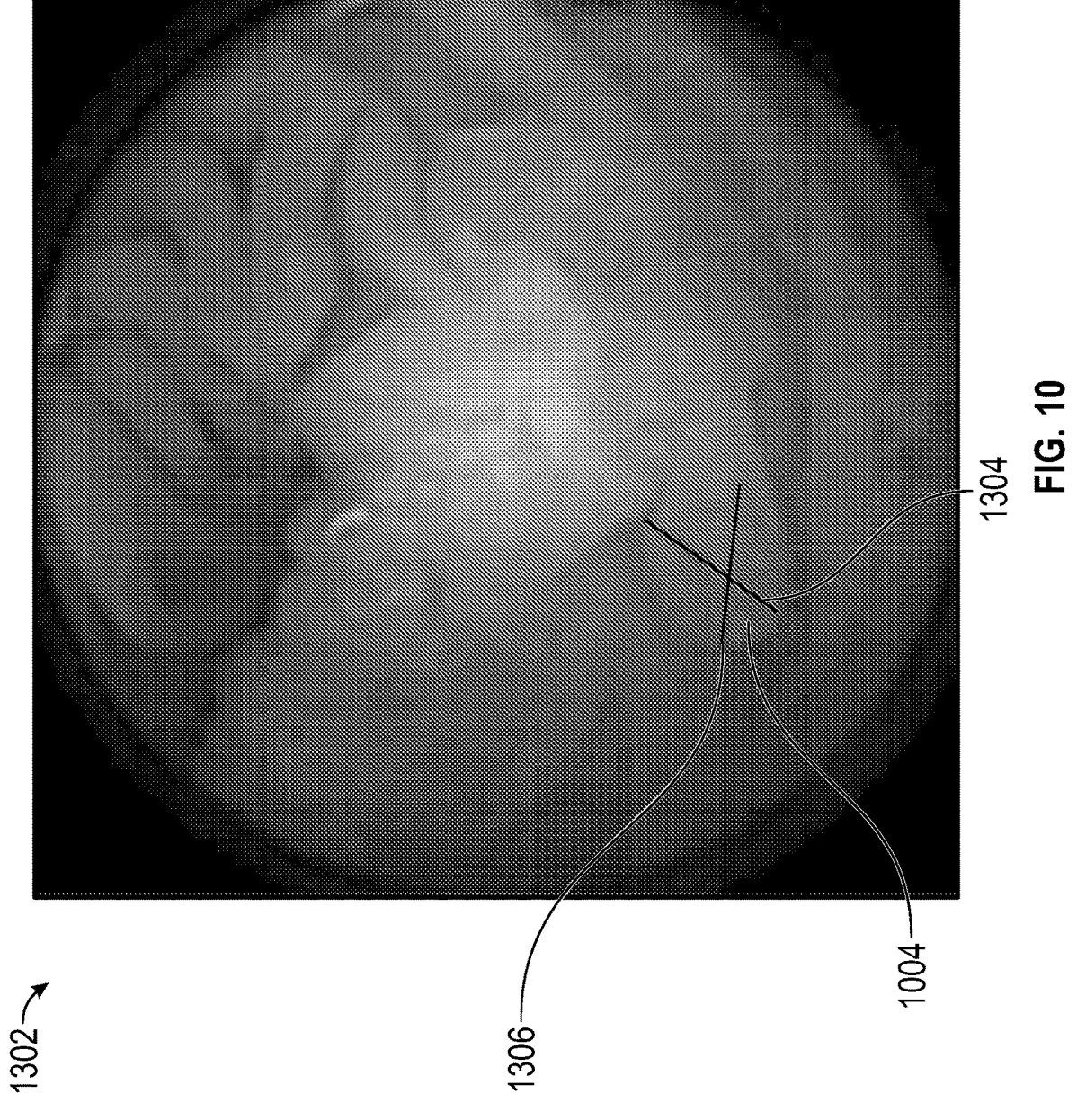
FIG. 10 shows the example image of FIG. 7 following completion of various steps of the method of FIG. 5, in accordance with aspects of the disclosure.

With reference to FIG. 10, an image 1302 is shown illustrating two exemplary most distant pairs and the corresponding 2D distances of the pairs 1304, 1306 as shown on the polyp 1004.

Figure 11:
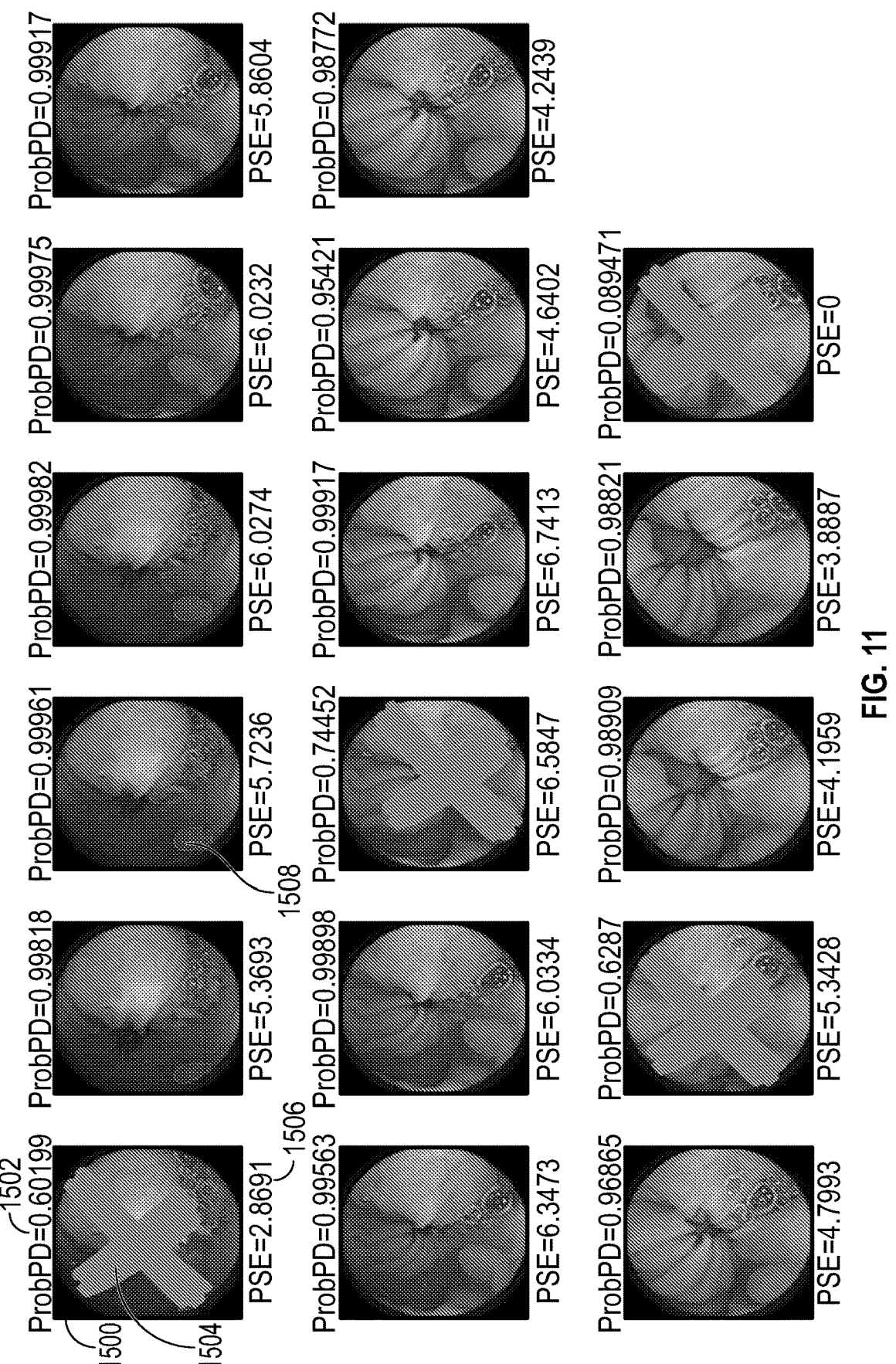
FIG. 11 shows a plurality of images showing the same suspected polyp, in accordance with aspects of the disclosure.

FIG. 11 illustrates a plurality of images 1500 of portions of the GIT showing the same polyp 1508 in the images. The plurality of images 1500 includes the probability 1502 from a polyp detector (e.g., a deep learning neural network) that a polyp is in the image, an estimated polyp size 1506 determined by the disclosed systems and methods, and an indication of whether an image should be excluded in the weighted estimated polyp size of method 900 based on either the probability 1502 and/or the estimated polyp size 1506 being below a predetermined threshold (e.g., the polyp size being too small).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A computer-implemented method for estimating a size of a polyp without human intervention using semantic segmentation by deep learning convolutional neural networks for polyp detection and localization followed by region property analysis to determine extreme peripheral points of the estimated polyp followed by size estimation, the computer-implemented method comprising:

accessing a number k of light images of at least a portion of a gastrointestinal tract (GIT) captured during a capsule endoscopy procedure using light, wherein k>1, wherein each light image of the unstructured light images is associated with a respective estimated size of a suspected polyp determined based on the respective light image, the estimated sizes of the suspected polyp comprising a first size value $size_1$ and a second size value $size_2$, wherein the light images are determined to include the same suspected polyp;

determining a weight of each light image of the light images indicative of a probability of the respective light image including a polyp, the weights comprising a first weight value $weight_1$ and a second weight value $weight_2$; and estimating a weighted polyp size for the suspected polyp based on the determined weights of the light images and based on the estimated sizes of the suspected polyp according to the light images, wherein the estimating the weighted polyp size comprises computing:

$$(weight_1 \cdot size_1 + weight_2 \cdot size_2).$$

2. The computer-implemented method of claim 1, further comprising identifying the accessed light images from a plurality of images of the GIT based on a machine learning system.

3. The computer-implemented method of claim 1, further comprising estimating the size of the suspected polyp in each light image of the light images that includes the suspected polyp.

4. The computer-implemented method of claim 1, wherein the weight of each light image of the light images is determined further based on a distance of the light image from a predefined light image.

5. The computer-implemented method of claim 1, wherein the weight of each light image of the light images is determined further based on a cleansing score of the light image.

6. The computer-implemented method of claim 1, wherein the weight of each light image of the light images is determined further based on: a distance of the light image from a predefined light image, and a cleansing score of the light image.

7. The computer-implemented method of claim 1, wherein the estimated sizes of the suspected polyp comprise a third size value $size_3$, wherein the weights comprise a third weight value $weight_3$, and wherein the estimating the weighted polyp size further comprises computing:

$$(weight_3 \cdot size_3),$$

such that the estimating the weighted polyp size comprises computing:

$$(weight_1 \cdot size_1 + weight_2 \cdot size_2 + weight_3 \cdot size_3).$$

8. An apparatus for estimating a size of a polyp without human intervention using semantic segmentation by deep learning convolutional neural networks for polyp detection and localization followed by region property analysis to determine extreme peripheral points of the estimated polyp followed by size estimation, the apparatus comprising:

at least one processor; and at least one memory having stored thereon instructions which, when executed by the at least one processor, cause the apparatus at least to perform:

accessing a number k of light images of at least a portion of a gastrointestinal tract (GIT) captured during a capsule endoscopy procedure using light, wherein k>1, wherein each light image of the light images is associated with a respective estimated size of a suspected polyp determined based on the respective light image, the estimated sizes of the suspected polyp comprising a first size value $size_1$ and a second size value $size_2$, wherein the light images are determined to include the same suspected polyp;

determining a weight of each light image of the light images indicative of a probability of the respective light image including a polyp, the weights comprising a first weight value $weight_1$ and a second weight value $weight_2$; and estimating a weighted polyp size for the suspected polyp based on the determined weights of the light images and based on the estimated sizes of the suspected polyp according to the light images, wherein the estimating the weighted polyp size comprises computing:

$$(weight_1 \cdot size_1 + weight_2 \cdot size_2).$$

9. A computer-readable medium having stored thereon instructions for estimating a size of a polyp without human intervention using semantic segmentation by deep learning convolutional neural networks for polyp detection and localization followed by region property analysis to determine extreme peripheral points of the estimated polyp followed by size estimation, the instructions, when executed by at least one processor of an apparatus, cause the apparatus at least to perform:

accessing a number k of light images of at least a portion of a gastrointestinal tract (GIT) captured during a capsule endoscopy procedure using light, wherein k>1, wherein each light image of the light images is associated with a respective estimated size of a suspected polyp determined based on the respective light image, the estimated sizes of the suspected polyp comprising a first size value $size_1$ and a second size value $size_2$, wherein the light images are determined to include the same suspected polyp;

determining a weight of each light image of the light images indicative of a probability of the respective light image including a polyp, the weights comprising a first weight value $weight_1$ and a second weight value $weight_2$; and estimating a weighted polyp size for the suspected polyp based on the determined weights of the light images and based on the estimated sizes of the suspected polyp according to the light images, wherein the estimating the weighted polyp size comprises computing:

$$(weight_1 \cdot size_1 + weight_2 \cdot size_2).$$

* * * * *